United States Patent [19]

Smith et al.

[11] Patent Number: 5,164,310

[45] Date of Patent: Nov. 17, 1992

[54] METHOD FOR TRANSFORMING PLANTS VIA THE SHOOT APEX

[75] Inventors: Roberta H. Smith, Hearne; Jean H. Gould, Bryan; Eugenio Ulian, College Station, all of Tex.

[73] Assignee: The Texas A&M University System, College Station, Tex.

[21] Appl. No.: 650,685

[22] Filed: Feb. 5, 1991

Related U.S. Application Data

[63] Continuation of Ser. No. 322,660, Mar. 13, 1989, abandoned, which is a continuation-in-part of Ser. No. 201,568, Jun. 1, 1988, abandoned.

[51] Int. Cl.[5] .................. C12N 15/00; C12N 5/04; A01H 1/06; A01H 4/00
[52] U.S. Cl. ..................... 435/172.3; 435/172.1; 435/320.1; 435/252.2; 435/240.4; 435/240.45; 800/205
[58] Field of Search ............ 435/172.3, 240.49, 320.1, 435/172.2, 172.1, 240.45, 252.2, 252.3; 800/200, 205, 235, 250, DIG. 24, DIG. 26, DIG. 9, DIG. 43, DIG. 55, DIG. 56, DIG. 58

[56] References Cited

PUBLICATIONS

Yadav (1986) Results & Problems in Cell Differentiation 12, Springer Verlag, Berlin.
Sharp et al. (1981) Proceedings of the Inter. Symp. of Genet. Engineering, Ed. O. J. Crocomo et al.
Graves et al. Plant Molecular Biology 7:43–50 (1986).
Kartha et al. (1981) Can. J. Botony. vol. 59–pp. 1671–1679.
Esau, (1967) *Plant Anatomy* Wiley & Sons Inc. p. 110.
de la Pena (1987) Nature 325:274–276.
Byrne et al. (1987) Plant Cell/Tissue & organ Culture vol. 8: pp. 3–15.
Stoebel et al. (1985) Nature vol. 318: pp. 624–629.
Braun (1959) PNAS pp. 932–938.
Braun (1962) Ann. Rev. Pl. Physiol, 13: 533–558.
Graves et al. (1988) J. Bacteriology pp. 2395–2400.
Ball (1980) Ann. Bot. p. 103.
Schrammeijer et al. (1990) Plant Cell Reports 9:55–60.
Hussey et al. (1989) Protoplasma 148: 101–105.
Raineri et al. (1990) Biotechnology vol. 8, pp. 33–38.
Binns et al. (1988) An. Rev. Microbiology 42: 575–606.
Bidney et al. (1992) Pl. Mol. Biol. 18: 301–302.
Feldman et al. (1987) Mol. Gen. Genetics 208: 1–9.
Christou et al. (1986) Pl. Physiology 82: 218–221.
Ulian et al. (1988) In Vitro Cellular & Dev. Biol. 24:9 pp. 951–954.
Fromm et al. (1986) Nature vol. 319 pp. 791–793.
Fahn (1974) *Plant Anatomy* Pergaman Press p. 574.
*The Encyclopedia Americana, International Edition* (1967) Plant & Plant Science-Anatomy, pp. 178–179.

*Primary Examiner*—Elizabeth C. Weimar
*Assistant Examiner*—Gary Benzion
*Attorney, Agent, or Firm*—Arnold, White & Durkee

[57] ABSTRACT

The invention relates to a novel method for transforming and rapidly regenerating plant tissue. The method employs target tissues which are the shoot apices thereby expanding the species range for transformation and reducing the risk of somaclonal variation.

10 Claims, 1 Drawing Sheet

METHOD FOR TRANSFORMING PLANTS VIA THE SHOOT APEX

This application is a continuation of Applicants' co-pending application Ser. No. 322,660 filed Mar. 13, 1989, now abandoned, which is a continuation-in-part of patent application Ser. No. 201,568 filed Jun. 1, 1988 now abandoned.

The present invention relates to a method for transforming plants with a high level of rapid regeneration and low risk of tissue culture-induced genetic variation. Specifically the method employs isolated shoot apices from seedling tissue, or axillary buds of intact plants as the target tissue for transformation and for subsequent use in the regeneration of plants.

BACKGROUND OF THE INVENTION

The lack of routine, repeatable regeneration from plant cell culture systems for agriculturally important crops is a major obstacle in the application of genetic engineering technology to plants. Additionally, as reported by Larkin and Scowcroft, Theor. Appl. Genet. 60, 197 (1981), the potential for somaclonal variation exists when plants are regenerated adventitiously in vitro. Somaclonal variants can result following *A. tumefaciens* mediated gene transfer. Somaclonal variation is the genetic variability observed in plants derived from a callus intermediate. This phenomenon is undesirable where it is essential to maintain the original genetic integrity of transformed plants.

*Agrobacterium tumefaciens* has been the preferred vector for leaf disk, epidermal peel or other explants in a cocultivation system for gene transfer. *A. tumefaciens* mediate gene transfer has been developed using members of the Solanaceae family because of the ease of manipulation of this family in culture and infectivity of Agrobacterium species for this family. Although many other dicotyledonous species are known to be suitable hosts for Agrobacterium, plants from only a handful of these species have successfully been transformed principally due to the lack of regeneration systems.

Development of the leaf disk transformation system by Horsch et al., Ann. Rev. Plant Physiol. 38, 467 (1987), allowed almost routine transfer of foreign genetic material, but only into a limited number of plant species. This model system was demonstrated using members of the Solanaceae family: petunia, tobacco and tomato species which are comparatively easy to regenerate from leaf explant material. The leaf disk technique overcame many of the problems inherent in the protoplast transformation systems, particularly the extended culture period required and the limited regeneration of plants from protoplasts.

The leaf disk system, however, is severely limited. The most serious limitation is that few plant species can be regenerated from leaf tissues. Even for some cultivated petunia varieties, regeneration from leaf disks is difficult. Another limitation of the leaf disk system is that adventitious shoot meristems differentiate from epidermal and subepidermal leaf tissues. Derivatives of the leaf disk method have been developed to include the use of seedling tissues in conjunction with induction of somatic embryogenesis, as well as callus followed by shoot induction. In each of these cases, however, the potential for somaclonal variation exists because the embryos, as well as the shoot meristem, must develop adventitiously.

Another system of plant transformation has been developed by Trinh et al., 5 Biotechnology, 1081 (1987). The system involves the use of the tobacco epidermal peel system and cocultivation with Agrobacterium. The benefit of this system was the direct production of flowers and seeds in eight weeks. Again, important concerns with this system are the limited adaptation of this technique to crop species and the potential for somaclonal variation, since the plants arise via adventitious organogenesis.

SUMMARY OF THE INVENTION

The present invention addresses the obstacles presented by previous techniques by using shoot apex tissue as the tissue subjected to gene transfer. Use of such a tissue permits rapid propagation of plants while perpetuating the unique clonal and genetic characteristics of the plant being transformed. Shoot meristem tissue, including shoot tip culture and axillary bud proliferation are preferred in the practice of the invention. The shoot apex is the most preferred explant for plant transformation as most herbaceous dicotyledon and monocotyledon plants can be regenerated into intact plants using this explant source. Shoot cultures also develop directly and rapidly into rooted plants. In addition to the shoot apex, other non-adventitious tissues such as the axillary bud can be used in the practice of this invention.

In applying the method of the invention to shoot apices, shoot apices excised from selected plants are cultured in an appropriate medium. After the apices have been excised or cultured for several days, the apices are exposed to a suitable vector such as *Agrobacterium tumefaciens*. The innoculated apices are then cultured for several more days. Following cultivation, the apices are then transferred to a selection medium to differentiate transformed from nontransformed plant tissues. Transformed tissues are then selected and recultured in a rooting medium. Rooted plants can then be grown under normal conditions.

This method permits rapid regeneration of transformed plants. Experiments with petunia for example have yielded results within six weeks. Plants produced by the above method have been selfed and the resulting seeds aseptically germinated. Ninety percent of the seedlings produced were found to possess the new inserted gene, verifying sexual transmission of the new genetic information.

Bacteria from the genus Agrobacterium are preferred in the practice of this invention, however, other vectors capable of genetic transformation in plants can be used to include other bacteria, plasmids, viruses, and DNA fragments.

DETAILED DESCRIPTION OF THE INVENTION

Figure 1:
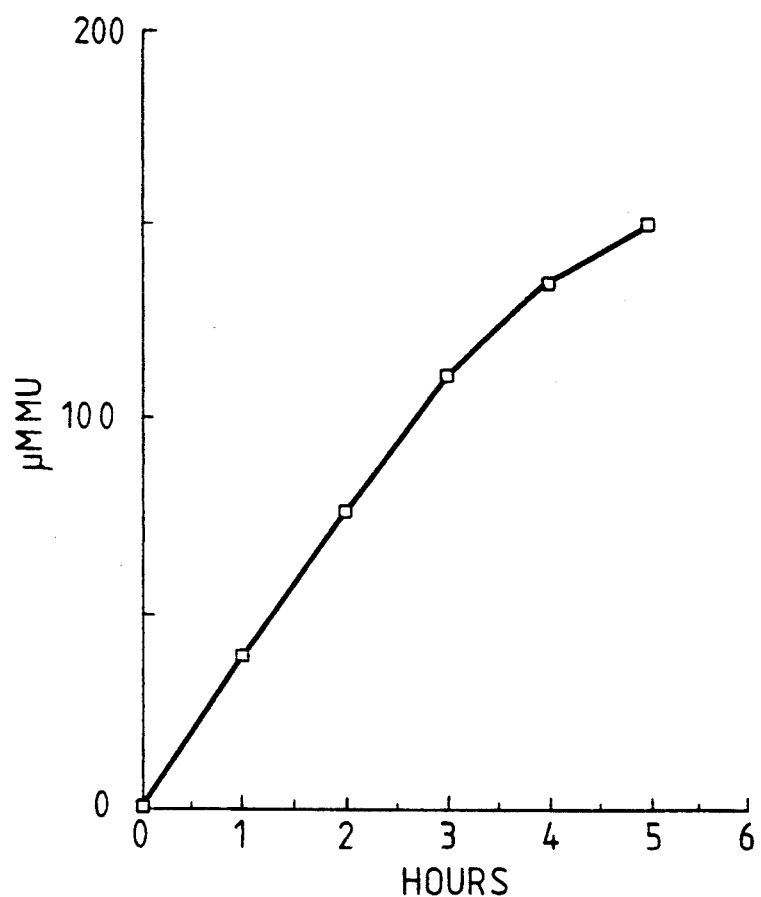
FIG. 1 shows the results of a fluorometic GUS assay of transformed plants indicating the course of GUS activity over 5 hours. The amount of methyl umbelliferone produced was quantified with a Kontron spectrofluorimeter. This shows the successful transformation of petunia using the method of this invention.

The discussion and examples which follow detail the best known method for performing the invention. It will be recognized that variations of this method may include different culture media or different vectors dependent upon the target plant species and the traits to be transferred into the target plants. Petunias, soybeans, alfalfa, sunflowers, cotton, wheat and corn were chosen as the target plants in the following examples, however, the method outlined below is adaptable to other plants capable of regeneration from shoot apices or axillary buds without significant experimentation or deviation from the spirit and scope of this invention.

The following examples merely illustrate the nature of the invention. It will be apparent to those skilled in the art that this method can be used for any dicotyledonous plant which can be regenerated from the shoot apex and which can be transformed by Agrobacterium. The method may also be modified to transform monocotyledonous species without departing from the scope and spirit of the invention.

While selection using kanamycin resistance is preferred, insertion of gene sequences coding for resistances to other antibiotics such as G418, neomycin, hygromycin or chloramphenical or to herbicides such as glyphosate can be used as well as other selectable genes known to those skilled in the art. Additionally, certain additives may be used to enhance successful infection of the shoot species. These include acetosyringone and certain opines such as, but not limited to octapine, nopaline and leucinopine.

EXAMPLE I

Germination of Explant Source

Seeds of the commercial petunia variety 'Rose Flash', an $F_1$ hybrid of Single Grandiflora and Deep Rose, were obtained from the Ball Seed Co., West Chicago, IL. The seeds were surface sterilized in 20% (v/v) commercial bleach to which a wetting agent such as Tween 20 or dishwashing detergent had been added, for thirty minutes. The seeds were then rinsed five times with sterile water.

The sterilized seeds were then aseptically germinated on Murashige and Skoog salts with 30% sucrose (w/v). The Murashige and Skoog salts were prepared as follows: Stock solutions of the following salts were prepared (in g/l of stock):

(1) Nitrates: ammonium nitrate ($NH_4NO_3$), 165; potassium nitrate ($KNO_3$), 190;

(2) Sulfates: magnesium sulfate ($MgSO_4$ $7H_2O$), 37; manganous sulfate ($MnSO_4$ $H_2O$), 1.690; zinc sulfate ($ZnSO_4$ $7H_2O$), 0.860; cupric sulfate ($CuSO_4$ $5H_2O$), 0.0025;

(3) Halides: calcium chloride ($CaCl_2$ $2H_2O$), 44; potassium iodide (KI), 0.083; cobalt chloride ($CoCl_2$ $6H_2O$), 0.0025;

(4) $PO_4$, $BO_3$, $MoO_4$ potassium phosphate ($KH_2PO_4$), 17; boric acid ($H_3BO_3$), 0.620; sodium molybdate ($Na_2MoO_4$ $2H_2O$), 0.025;

(5) Na2FeEDTA: ferrous sulfate ($FeSO_4$ $7H_2O$), 2.784; ethylene-diaminetetraacetic acid, disodium salt ($Na_2EDTA$), 3.724.

Ten ml of each of the five above stocks were added to one liter of medium prepared.

Excision and Innoculation of Shoot Apices

After one week of germination shoot apices were excised from the plants germinated from the above procedure. The apices were 0.3×0.6 mm in size and consisted of the apical dome and two primordial leaves. The excised shoot apices were then cultured on the Murashige and Skoog salts described above with the following added components, 0.1 mg/l N6-benzyladenine, 30,000 mg/l sucrose and 2,000 mg/l gel-rite obtained from KC Biological, Kansas City, Mo.

After two days of culturing, isolated shoot apices were inoculated with a 5 µl drop of *Agrobacterium tumefaciens* suspension described below. The plates were left open in a transfer hood until the drop had dried. The culture plate with the shoot apices was then sealed and incubated for two days at 25° C., with a light to dark period of 16:8 hours.

Preparation of *A. Tumefaciens* for Innoculation

The Agrobacterium suspension used to innoculate the shoot apices was prepared as follows: A binary vector pRGUS2 was created by Dr. Terry Thomas of Texas A&M University by cloning a BamHI—SstI restriction fragment containing the beta-glucuronidase (GUS) coding region, isolated from pGUS1 into the polylinker site of pROK2, an expression vector derived from pROK1(20) by the insertion of a polylinker. This placed the GUS gene between the CaMV 35S promoter and the nopaline synthase polyadenilation signal in the T-DNA. The pRGUS plasmid was conjugated from *E. coli* strain HB101 into the avirulent *A. tumefaciens* strain LBA 4404 as described in Simpson et al, Plant Mol. Biol. 6:403–415. The result was a strain of *A. tumefaciens* which contained the genes for kanamycin resistance and for beta-glucuronidase. This permitted easy differentiation and detection of transformed tissues.

The *A. tumefaciens* LBA 4404 (pRGUS 2) was grown in a medium prepared as follows: A 100 ml salt solution was prepared comprising 3.9 g dibasic potassium phosphate $0.3H_2O$; 1 g sodium monobasic phosphate, 1 g $NH_4CL_2$ and 0.15 g potassium chloride. The salt solution was then autoclaved at 121° C., and 18 psi for 15 minutes. A separate, 900 ml media solution was prepared containing 0.5 g/l. sucrose; 13 mg calcium chloride, 0.5 g/l magnesium sulfate, 10 µl ferric sulfate stock (250 mg/ml $FeSO_4.7H_2O$) Where the bacterium was cultured in stock cultures, 15 g of agar was added to the media solution, for suspension or liquid cultures, agar was omitted. The media solution was then autoclaved for 25 minutes and cooled. The salt and media solutions were then combined and 50 mg of kanamycin was added to the medium. *A. tumefaciens* LBA 4404 (pRGUS 2) was grown on 3 ml of medium for 2 days. The medium and cultured *A. tumefaciens* was then used to innoculate the shoot apices in the manner described above.

Selection and Cloning of Transformed Apices

Following innoculation and incubation, the shoot apices were transferred to fresh medium comprising the Murashige and Skoog salts described above with 0.1 mg/l N6-benzyladenine, 30,000 mg/l sucrose and 2,000 mg/l gelrite and cultured for two additional days. The apices were then subcultured onto a medium comprising Murashige and Skoog salts as described above; 0.1 mg/l N6-benzyladenine, 30,000 mg/l sucrose, 2,000 mg/l gel-rite, 200 mg/l kanamycin and 500 mg/l carbenicillin, the latter obtained from Sigma, St. Louis, Mo.).

After three weeks of incubation, all explants had grown. Untransformed tissues exhibited bleaching in the presence of 200 mg/l kanamycin medium. Transformed shoots appeared as green regions at the base of bleached leaves. The bleached leaves were then removed and the green tissue recultured onto medium containing 100 mg/l kanamycin. Single green shoots developed from the explants after 1 week and were transferred to rooting medium containing Murashige and Skoog salts, 3% sucrose, 100 mg/l kanamycin and 500 mg/l carbenicillin. All the explants exhibited root production.

The rooted plants were then assayed for the presence of the GUS gene as follows. Approximately 50 mg of plant tissue was homogenized in an Eppendorf tube with a pestle in 200 μl of 50 mM NaPO$_4$, pH 7.0, 10 mM EDTA, 0.1% Triton X-100, (Sigma Chemical) 0.1% Sarkosyl, (Sigma Chemical) 10 mM beta-mercaptoethanol. One hundred μl of the extract were added to 100 μl of 2mM 4-methyl umbelliferil glucuronide dissolved in the same buffer. The reaction was incubated at 37° C. for 5 hours and stopped with 1 ml of 0.2 M Na$_2$CO$_3$. The production of methyl umbelliferone was quantified with a Kontron spectro fluorimeter at hourly intervals. The result of the assay can be seen in FIG. 1.

EXAMPLE 2

Comparison of Shoot Apex and Leaf Disk Culture Systems.

A comparison was made between the leaf disk culture method and the shoot apex method of the present invention.

One hundred thirteen shoot apices from *Petunia hybrida* cv 'Rose Flash' were co-cultivated with *A. tumefaciens* and cultured on selective medium as described above. Shoots with green bases were isolated (Table 1) and transferred to medium containing 100 mg kanamycin /l for 1 week and subsequently transferred to rooting medium as described above.

Leaf disks were also taken from *Petunia hybrida* cv 'Rose Flash' and transformed according to the procedure described by Horsch et al. Science 227, 1229 (1985). The selective media was composed of MS medium containing 1.0 mg/l N6-benzyladenine, 0.1 naphthalene mg/l acetic acid, 100 mg/l, 200 mg/l or 300 mg/l kanamycin and 500 mg/l carbenicillin. Table 1 reflects the results achieved.

TABLE 1

| Kanamycin Concentration:mg/l | Test Disk 100 | Leaf Disk 300 | Shoot Apex 200 |
|---|---|---|---|
| Callus Production | 13/28[a] (46%) | 25/25 (100%) | 3/113 (3%) |

TABLE 1-continued

| Kanamycin Concentration:mg/l | Test Disk 100 | Leaf Disk 300 | Shoot Apex 200 |
|---|---|---|---|
| Shoot Production | 13/28 (46%) | 0/25 (0%) | 7/113 (6%) |
| Shoots Rooting | 2/13 (15%) | — | 5/7 (71%) |
| Plants GUS Positive | 2/2 (100%) | — | 5/5 (100%) |

[a]Number of original explants.

Callus production from leaf disk explants was high on 100 and 300 mg kanamycin /l (46% and 100%) and very limited from shoot apex explants (3%). Shoot production from shoot apex explants cultured on kanamycin was low (6%) as compared with that of leaf disk (46%). Although the regeneration of leaf disks and shoot apices are different, this is an indication that the shoots that formed from shoot apex explants were more likely to be transformed (71%) than those formed using the leaf disk explant (15%).

As can be seen from this data, the key difference between the two techniques is the almost universal regeneration of plants from the shoot apex. Similar results can be achieved with lateral bud explants.

To determine if chimeric plants were produced using the shoot apex explant method, GUS assays of the type described above were conducted on the leaves, petals, ovaries, and ovule tissues from various regions of GUS positive plants. All tissues assayed showed GUS gene expression.

EXAMPLE 3

Stability of Incorporation

The important issue in plant transformation is stable incorporation of the trait in the germ line and expression in the progeny. If this occurs, the question of the chimeric nature of the primary transformants is less of a concern.

To determine if the trait had been successfully passed to the next generation in Example 2, flowers of GUS positive plants were selfed. Three hundred and seven seeds from twenty flowers of four different GUS positive plants were germinated as described above and seedlings were assayed for GUS activity. As shown in Table 2, approximately 90% of the seedlings were GUS positive.

TABLE 2

| Plant (95%) | Flower | Number of Seeds | GUS+ | GUS− | % Expression (GUS+/totals) | Confidence limits |
|---|---|---|---|---|---|---|
| 1 | 1 | 15 | 14 | 1 | 93.3 | (73–100) |
|   | 2 | 15 | 14 | 1 | 93.3 | (73–100) |
|   | 3 | 15 | 14 | 1 | 93.3 | (73–100) |
|   | 4 | 15 | 13 | 2 | 86.7 | (60–98) |
|   | 5 | 15 | 15 | 0 | 100.0 | (78–100) |
|   | Total | 75 | 70 | 5 | x = 93.3 |  |
| 2 | 1 | 15 | 14 | 1 | 93.3 | (73–100) |
|   | 2 | 15 | 13 | 2 | 87.0 | (60–100) |
|   | 3 | 23 | 20 | 3 | 87.0 | (65–100) |
|   | 4 | 16 | 14 | 2 | 87.5 | (61–100) |
|   | 5 | 13 | 12 | 1 | 92.0 | (58–100) |
|   | Total | 82 | 73 | 9 | x = 89 |  |
| 3 | 1 | 15 | 13 | 2 | 86.7 | (58–98) |
|   | 2 | 15 | 15 | 0 | 100.0 | (78–100) |
|   | 3 | 15 | 14 | 1 | 93.3 | (73–100) |
|   | 4 | 15 | 14 | 1 | 93.3 | (73–100) |
|   | 5 | 15 | 13 | 2 | 86.7 | (60–98) |
|   | Total | 75 | 69 | 6 | x = 92 |  |

TABLE 2-continued

| Plant (95%) | Flower | Number of Seeds | GUS+ | GUS− | % Expression (GUS+/totals) | Confidence limits |
|---|---|---|---|---|---|---|
| 4 | 1 | 15 | 10 | 5 | 66.6 | (37–88) |
|   | 2 | 15 | 12 | 3 | 80 | (52–97) |
|   | 3 | 15 | 11 | 4 | 73 | (43–93) |
|   | 4 | 15 | 12 | 3 | 80 | (52–97) |
|   | 5 | 15 | 12 | 3 | 80 | (52–97) |
|   | Total | 75 | 57 | 18 | x = 76 |  | x = average value.

Referring to Table 3, calculated Chi square values for the expression of the GUS gene in the progeny on one plant indicated a 3:1 segregation pattern of a monohybrid which indicates insertion on a single chromosome. Chi square values for 3 of the plants indicated a 15:1 segregation pattern of duplicate dominant dihybrid segregation which indicates insertion of copies on two independent chromosomes.

TABLE 3

| | Segregation Ratio | | | |
|---|---|---|---|---|
| | (3:1) | | (15:1) | |
| | $x^{2a}$ | P | $x^2$ | P |
| Plant 1 | 13.44 | <0.001 | 0.03 | >0.80 |
| Plant 2 | 9.84 | <0.01 | 3.12 | >0.05 |
| Plant 3 | 11.56 | <0.001 | 0.39 | >0.5 |
| Plant 4 | 0.04 | >0.8 | 40.32 | <0.01 |

Data calculated with df = 1; at the 95% confidence level.

EXAMPLE 4

Two additional petunia cultivars, V23xR51 from T. Gerats and 'White Flash' (F1 hybrid: Grandiflora×Pure White Ball Seed, Co., Chicago, Ill.) were transformed using the shoot apex method described above. As shown in Table 4, the transformation of these strains achieved results similar to those found in Table 1. This indicates that the procedure can be used for other plant varieties with similar success.

The transformed *Petunia hybrida* strain V23XR51 were selfed and the seeds collected and cultivated. As shown in Table 5, 70% to 90% of the progeny exhibit GUS activity indicated that the gene was successfully transmitted to the next generation.

TABLE 4

Comparison of transformation of *Petunia hybrida* cv. 'V23XR51' and 'White Flash' using the leaf disk and shoot apex system as in Example 1.

| [Kanamycin] mg/l | 100 | Leaf Disk 300 | Shoot Apex 200 |
|---|---|---|---|
| V23xR51 | | | |
| No. of Explants | 26 | 34 | 18 |
| Callus Produced | $x^a$ | 14 | 0 |
| Shoots Produced | — | 14 | 8 |
| Shoots Rooting | — | 9 | 8 |
| Plants GUS Positive | — | 5 | 2 |
| White Flash | | | |
| No. of Explants | 30 | 33 | 102 |
| Callus Produced | 30 | 12 | 0 |
| Shoots Produced | 0 | 11 | 10 |
| Shoots Rooting | — | 11 | 4 |
| Plants GUS Positive | — | 11 | 4 |

$a_x$ = Number of shoots was very large and not counted.

TABLE 5

Segregation for the GUS gene in the progeny of self pollinated GUS + plants of cv. 'V23xR51' as in Example 2.

| Plant | Number of Seeds | GUS(+) | GUS(−) | % Expression |
|---|---|---|---|---|
| 1 | 40 | 28 | 12 | 70.0 |
| 2 | 40 | 36 | 4 | 90.0 |

This data, coupled with the data shown in Example 3 highlights one of the key features of the method of the invention - the transformation of the germ cells as well as the somatic cells of the target plant which permits inheritance of the new trait by future generations. Techniques used by others produce sterile plants, failure to transform the germ cells or the transformation of the germ cells occur at a much lower percentage resulting in fewer progeny expressing the desired trait.

Chi Squared values for the expression of the GUS gene in the progeny of the transformed 'V23xR51' plants indicated a 3:1 segregation of a monohybrid which indicates insertion on a single chromosome. Chi squared values for the other plant indicated a 15:1 segregation pattern of duplicate dominant dihybrid segregation which indicates insertion of copies of the GUS gene on two independent chromosomes.

TABLE 6

Evaluation of the segregation pattern of GUS expression in progeny of transformed plants of cv. 'V23xR51'

| | Segregation Ratio | | | |
|---|---|---|---|---|
| | (3:1) | | (15:1) | |
| Plant | $x^{2a}$ | p | $x^2$ | p |
| 1 | 0.533 | >0.30 | 38.5 | <0.01 |
| 2 | 4.8 | <0.05 | 0.96 | >0.30 |

Data calculated with df = 1; at the 95% confidence level.

EXAMPLE 5

Transformation via the shoot apex has also been employed with cotton, specifically *Gossypium hirsutum*, var. Coker 312. Tamcot CAB-CS. and *Gossypium barbadense*, var. Pima 5-6. The steps employed were the same as described above with the following variations.

Seeds were disinfected by rinsing them with distilled water for 10 minutes and then soaked in 20% commercial bleach with 1 drop of Tween 20 for 15 minutes. The seeds were then rinsed three times with sterile water.

Following disinfection, the seeds were transferred to sterile petri plates chalazal end down. Five seeds were placed on each plate. The plates contained a solution containing MS halides and solidified with 0.8% agar. The plates were incubated unsealed in darkness at 30° C. for four days. The plates were then subjected to a 16 hour day regimen for one day prior to isolation.

To ensure that the shoot apices were excised from plants at similar stages of development, the most uniform populations of seedlings were used. Slower germinating or contaminated seedlings were discarded.

Shoot apices were isolated from 5 day old seedlings with the aid of a dissecting microscope. In some cases, sterile hypodermic needles, 22 and 27 gauge, mounted on a plastic syringe casing were employed to accomplish the dissection.

The apex was excised by first removing one of the two cotyledons at its base. The shoot region was then removed from the seedling. The base of the shoot region was then trimmed to expose the basal face of the apical meristem. A modification of this technique was also used to remove the largest leaf and underlying tissue exposing the lateral face of the apical meristem as well as the basal face.

Shoot apices isolated from 3 to 4 day old seedlings consisted of the meristematic dome and two primordial leaves. Where the seedlings were older (5 to 7 days) the apices often contained more than the two leaf primordia.

The isolated apices were then cultured on a basal MS medium (described below) without hormones, at 28°–30° C. under 16-hour photo period. Light was provided using a continuation of Gro-Lux ® and cool flourescent lights at $50\mu$ E/m$^2$ sec. The apices were recultured onto fresh medium.

The medium comprised MS basal salt formulation described by Murashige & Skoog (op. cit. Murachige & Skoog, 1962) with the following additions: Sucrose, 15,000 mg/l; thiamine 6.4 mg/l; TC agar, 8,000 mg/l. Prior to use, the medium was sterilized by standard autoclaving methods and dispensed into sterile petri plates.

The apices were innoculated with *Agrobacterium tumefaciens* within two days of excision. Innoculation was accomplished by scraping the bacteria from the culture plate and applying this plaque to the cut surfaces of the shoot apices using either a hypodermic needle or a toothpick.

The apices were innoculated with one of two strains of *A. tumefaciens*. The first is strain LBA 4404 "GUS2" described above. The second is strain EHA1 which harbors a similar Ti plasmid as in GUS2. This plasmid was inserted into the EHAI strain and named "GUS$_3$" by Dr. T. McKnight of Texas A&M University. Strain EHA1 is believed to contain a hyper virulent region which increases the host range of *A. tumefaciens*.

In addition to the use of *A. tumefaciens* strain EHA1, the following additives were used to enhance successful infection: acetosyringone, 10–30 $\mu$M; and nopaline, 10–100 $\mu$M. (Veluthambi et al. submitted).

After two day's contact with *A. tumefaciens*, the explants were transferred to media containing 500 mg/l carbenicillin for one week. The explants were then transfered to media containing 7.5 mg/l kanamycin and 500 mg/l carbenecillin for another week. Finally, the explants were transferred to media containing carbenecillin 500 mg/l weekly.

When shoots contained four or more leaves the shoot bases were dipped in sterile rootone and transferred to sterile vermiculite in 3 inch clay pots and covered.

The explants and plantlets were assayed for the GUS gene as described above and were found to be GUS positive.

EXAMPLE 6

Sunflower, *Heleanthus annus*, var. Triumph 560. Seeds were germinated shoots isolated and incubated with *A. tumefaciens* EHAI, acetosyringone and nopaline (1) using the procedures described for cotton with the following modifications. The seeds were incubated for 2–3 days prior to shoot isolation. The Basal medium described for cotton, was supplemented with 1 mg/l IAA (indoleacetic acid).

Four sunflower plants flowered and produced seed. These seeds were germinated and many of the progeny seedlings were GUS positive.

EXAMPLE 7

Soybean, *Glycine max*, var. Dowling & Bragg. Sterilized seeds were allowed to germinate for 1 day and then the plumule was excised and cultured as described above. Shoot apices were also obtained from seeds which had been allowed to embibe water for 1 hour.

The culture media used were the same as that used for cotton except that the media used for shoot cultivation was supplemented with 0.1 mg/l kinetin to promote growth of the apices and 1.0 mg/l kinetin was added to promote adventitious shoot production.

Co-cultivation with *A. tumefaciens* EHAI, nopaline and acetosyringone was the same as for cotton above.

Following 2 days of co-cultivation with Agrobacterium, explants were transferred to media containing 25 or 50 mg/l kanamycin and 500 mg/l carbenicillin for 1 week. The explants were then transferred to hormone free media with 500 mg/l carbenicillin.

Spontaneous rooting was observed in many of the explants grown on media containing carbenicillin. Those explants not exhibiting roots were dipped in sterile rootone. The plants were then aseptically transferred to sterile vermiculite in 3 inch pots and covered.

A significant number of shoots were found to be GUS positive when grown in culture. Of the seedlings which survived transfer to soil, all were GUS positive.

EXAMPLE 8

Alfalfa, *Medicago sativa* var. Southern Special. Seeds were germinated and shoots isolated as described for cotton. Tissues were co-cultivated with *A. tumefaciens* EHAI, acetosyringone and nopaline.

Several GUS positive tissues were produced in vitro and 10 plants have been established in pots. Of these, at least four are positive for GUS.

EXAMPLE 9

Seeds to corn (variety Funks 6-90) and wheat (variety chinese spring), were rinsed with distilled water 10 minutes, soaked in 20% commercial bleach which included one drop of tween 20 for 15 minutes and rinsed three times in sterile water. The disinfected seeds were transferred to media containing MS halides and sulfates and solidified with 0.8% agar. The embryo region of the seed was placed in contact with agar. Unsealed plates were incubated in darkness at 30° C. for one day.

Shoot apices were isolated with the aid of a dissecting microscope. The leaf and underlying tissue were excised exposing the lateral face of the apical meristem as well as the basal face.

Isolated apices were cultured on a basal MS medium without hormones. Tissues were recultured onto fresh media weekly. Medium consisted of the MS basal salt forumulation (Murashige & Skoog, 1962) and the following in mg/l); sucrose 15,000; thiamine 0.4; TC agar, 8,000. The media were sterilized by autoclaving under standard conditions and dispensed into sterile plastic petri dishes. Cultures were maintained at 28°–30° C., for 16 hours using a combination of Gro-lux and cool white fluorescent lights, 50 µE/m2sec.

Shoot apex explants were either innoculated the day of isolation, or one and two days after isolation. *Agrobacterium tumefaciens*, strain EHA1 containing the "GUS3" construct from Dr. Tom McKnight, was used. This strain is supposed to contain a hyper-active virulence region which may increase the range of species infected (and transformed) by this strain (Tom McKnight, personal communication). The Agrobacteria were scraped from a confluent plate, innoculated 2-3 days previously containing appropriate growth media and antibiotic. The cut surfaces of the shoot species were innoculated with Agrobacterium with a sterile hypodermic needle or sterile toothpick.

In addition to use of the hyper-virulent "GUS3" strain of *Agrobacterium tumefaciens*, nopaline and acetosyringone were mixed with Agrobacterium prior to the innoculation step to increase virulence and trigger other responses associated with successful infection.

After two days of contact with Agrobacterium, the explants were transferred to media containing 500 mg/l carbenicillin for one week; then transferred to media containing 7.5 mg/l kanamycin and 500 mg/l carbenicillin for one week; and finally transferred to new media containing 500 mg/l carbenicillin at weekly intervals.

Developing corn and wheat shoots rooted spontaneously after two or three weeks.

As described in *Ulian et al.*, 1988. Corn and other monocots apparently contain an enzyme which will cleave the GUS substrate, producing a weak positive reaction. This weak GUS positive response in monocots is therefore not indicative of successful transformation. A strong GUS positive response, such as has been observed with some of the corn and wheat tissues may be indicative of successfuly transformation.

DNA was extracted according to Rogers and Bendich (1985, Plant Molec. Biol. 5:69-76), restricted using HindIII (Boehringer Mannheim Inc.) according to manufacturer's directions and separated by electrophoresis overnight. Transfer of DNA from gel to nylon filter was done according to Southern (1975, J. Molec. Biol. 98:503), using the alkaline transfer modification of Reed and Mann (1985, Nucleic Acid Res. 13:7207-7221). DNA was hybridized to $^{32}$P-labeled GUS probe consisting of the $^{35}$S promoter, GUS sequence and polyadenelyation coding regions, described previously. Southern analysis of the corn plants confirmed successful transformation.

What we claim:

1. A method of transforming excised shoot apical tissue comprising:
    a) excising shoot apical tissue consisting essential of the apical dome and two or more primordial leaves,
    b) placing said excised tissue in a suitable growth medium,
    c) inoculating said apical tissue with *Agrobacterium tumefaciens* to transform said tissue.

2. The method of claim 1 wherein said shoot apical tissue is an axillary bud.

3. The method of claim 1 with the added step of adding acetosyringone and an opine during the inoculation step.

4. The method of claim 3 wherein the opine is nopaline.

5. The method of claim 1 wherein the *Agrobacterium tumefaciens* comprises a hypervirulent strain.

6. The method claim 1 wherein the shoot apical tissue is excised from a dicot.

7. The method of claim 1 wherein the shoot apical tissue is excised from a monocot.

8. A method for transforming an excised shoot apex comprising:
    a) excising a shoot apex,
    b) placing said apex in a suitable growth medium,
    c) inoculating said apical tissue with *Agrobacterium tumefaciens* to transform said tissue.

9. The method of claim 8 wherein the shoot apex is excised from a dicot.

10. The method of claim 8 wherein the shoot apex is excised from a monocot.

* * * * *

UNITED STATES PATENT AND TRADEMARK OFFICE
CERTIFICATE OF CORRECTION

PATENT NO. : 5,164,310
DATED : November 17, 1992
INVENTOR(S) : Roberta H. Smith, Eugenio Ulian and Jean H. Gould It is certified that error appears in the above-indentified patent and that said Letters Patent is hereby corrected as shown below:

Column 3, line 52 add --;-- between "$MoO_4$" and "potassium".

Column 4, line 8 delete "." after "C" and before the comma.

Column 4, line 32 delete "0" after "phate" and before ".$3H_2O$".

Column 4, line 34 delete "." after "C" and before the comma.

Column 5, Table 1, line 45 delete "Test" and replace with --Leaf--.

Column 6, Table 1, line 3 delete "Test" and replace with --Leaf--.

Signed and Sealed this

Second Day of November, 1993

Attest:

BRUCE LEHMAN

Attesting Officer

Commissioner of Patents and Trademarks